United States Patent [19]
Lesniak et al.

[11] Patent Number: 4,826,880
[45] Date of Patent: May 2, 1989

[54] IMMOBILIZING PARTICULATE ABSORBENTS BY CONVERSION TO HYDRATES

[75] Inventors: John M. Lesniak, Hazlet; Franklin Boardman, Englishtown; Wayne G. Koci, Monmouth Junction, all of N.J.; James E. McCann, Warrington, Pa.

[73] Assignee: Johnson & Johnson, Inc., New Brunswick, N.J.

[21] Appl. No.: 98,650

[22] Filed: Sep. 21, 1987

[51] Int. Cl.$^4$ .................................................. C08J 9/36
[52] U.S. Cl. .......................................... 521/53; 521/55; 427/385.5; 427/212; 427/213.3; 427/213.31; 427/213.33; 427/222; 428/481; 428/482; 428/483; 428/500; 428/507; 428/509; 428/515; 428/516; 428/532; 428/533; 525/63
[58] Field of Search .................. 427/385.5, 212, 213.3, 427/213.31, 213.33, 222; 428/481, 482, 483, 500, 507, 509, 515, 516, 533, 532; 525/63; 521/53, 55

[56] References Cited

U.S. PATENT DOCUMENTS

| | | | |
|---|---|---|---|
| 4,090,013 | 5/1978 | Ganslaw et al. | 526/15 |
| 4,190,563 | 2/1980 | Bosley et al. | 260/17.4 |
| 4,354,901 | 10/1982 | Kopolow | 162/158 |
| 4,410,571 | 10/1983 | Korpman | 427/385.5 |
| 4,444,830 | 4/1984 | Erickson | 428/246 |
| 4,524,186 | 6/1985 | Nagase | 525/328.8 |
| 4,605,401 | 8/1986 | Chmelir et al. | 604/368 |

Primary Examiner—John Kight
Assistant Examiner—S. A. Acquah
Attorney, Agent, or Firm—Lawrence D. Schuler

[57] ABSTRACT

The invention relates to absorbent compositions, to methods for handling and immobilizing particulate absorbents, and to absorbent articles produced from the absorbent compositions. Absorbent materials such as cross-linked, water-insoluble and water-swellable particulate polymers are immobilized and safely handled by adding thereto an aqueous liquid such as water or saline in amounts sufficient to form hydrates in which the water comprises from 20% to 80% by weight of the total hydrate. The hydrates may be extruded, sprinkled, or sprayed and can be incorporated into absorbent articles such as diapers and tampons by conventional means. The hydrates unexpectedly increase the total water absorbency of the absorbent on a dry basis.

25 Claims, No Drawings

IMMOBILIZING PARTICULATE ABSORBENTS BY CONVERSION TO HYDRATES

BACKGROUND OF THE INVENTION

The present invention relates to absorbent compositions, a method for handling and immobilizing particulate absorbents and absorbent articles produced therefrom.

Absorption of mobile aqueous liquids have conventionally been accomplished by the use of sponge or batting. More recently, water-insoluble but water-swellable polymers having high absorptive capacity have been developed for immobilizing water and aqueous fluids. These polymers are particulate, i.e., pulverulent or granular and have no structural integrity. They are frequently referred to in the art as "superabsorbents", "hydrogels" or "hydrocolloids" and have been incorporated in the cellulosic absorbent structure of diapers, sanitary napkins and other absorbent articles to increase their absorptive efficiency. The expected advantage of incorporating these particulate materials is diminished by the shifting of the particulate materials generally requiring special construction to immobilize them within the structure of the articles.

These particulate absorbents also present a health hazard to both the manufacturers and users because the particulates can be inhaled and swell inside the respiratory passages on contact with water vapor or liquid.

In an effort to overcome these disadvantages methods of treating such particulate polymers with liquids to immobilize them have been described in the art.

For example, in U.S. Pat. No. 4,410,571 immobilized superabsorbent compositions are described which are prepared by mixing a water-insoluble, water-swellable polymer absorbent and a liquid polyhydroxy organic compound such as glycerol or ethylene glycol. In this manner the superabsorbent is converted to a non-particulate immobilized form which can be foamed and is rendered self-supporting.

In U.S. Pat. No. 4,605,401, an absorption material is provided consisting of an absorbent permanently fixed on or in a support material obtained by treating the support material with a partially water-softened absorbent followed by drying. The preferred absorption material is an absorbent softened with an organic solvent containing up to 60% water.

U.S. Pat. No. 4,444,830 deals with an aqueous polymer solution containing from 5% to 60% by weight of polymer which is formulated into an absorbent composition. The aqueous polymer solution is coated on a base fluffing material, dried and the dried coated substrate is disintegrated into an absorbent hydrophilic fluff.

SUMMARY OF THE INVENTION

The present invention provides a method of safely handling or immobilizing water insoluble, water swellable absorbents by employing an aqueous liquid such as water as the treating medium to form an absorbent hydrate.

It has been found that water alone is an excellent adjunct for the absorbent rendering it safe to handle, and significantly reducing the cost of treatment of the absorbent in relation to organic liquids hereinbefore described. It has also been found that absorbent hydrates comprising water and absorbent according to the present invention can be formed which increase the water absorbency or retention capacity of the super-absorbent under pressure rather than reducing such absorbency or retention as might be expected.

The hydrates are formed by merely adding an aqueous liquid such as water or saline to the super-absorbent with mixing in amounts sufficient to comprise from 20% to 80% by weight of total composition. The resulting hydrates may be extrudable and can be incorporated into absorbent articles by conventional extrusion techniques, or may be sprinkled or sprayed onto absorbent articles.

DETAILED DESCRIPTION OF THE PREFERRED EMBODIMENTS

According to the invention, the addition of water to an absorbent material immobilizes the absorbent material rendering it safe to handle. When the absorbent material is mixed with water it can be incorporated into absorbent products such as diapers, tampons and the like. The hydrates are themselves absorbent and based on the dry superabsorbent content of the hydrate may absorb more water than dry absorbent alone. When incorporated into absorbent material such as fluffy wood pulp they retain more water than the fluflly wood pulp alone and almost as much as dry absorbent incorporated into the pulp.

The hydrates can be extruded without expanding to a uniform consistency and can be applied to a temporary or ultimate surface. The ultimate surface is hereinafter referred to as the substrate. For making a film, sheet, or coated substrate, any method of application conventionally employed for coating or preparing films, e.g. knife-coating, spray-coating, reverse-roll coating, gravure-coating, cold extrusion coating or casting, sprinkling and the like, may be employed. Preferred methods are cold extrusion coating and sprinkling.

When use as a coating on a substrate is contemplated, the substrate is of materials generally employed for absorbent articles, such as cellulose, vinyl films, polypropylene, polyester, polyethylene, nylon, metal foils, elastomers, cloth, nonwovens of various fibers, and the like. Coating on a substrate may be of the entire surface of the substrate, in strips, in rows, or in any other predetermined pattern.

The amount of water used in forming the hydrates of the invention may vary from about 20% to 80% by weight of the total weight of the composition and preferably from about 30% to 50% by weight of the composition, the remainder being absorbent.

The hydrates are prepared quite easily by merely combining the absorbent and water with mixing until a tacky, agglomerate is formed.

The actual amounts of absorbent in the hydrates within the scope previously indicated is dependent on the level of absorption required in the ultimate environment. Thus, if the absorption is to be accomplished by a diaper, and the substrate is a diaper pad, the hydrate will contain absorbent sufficient to supply the desired absorptive capacity in the pad substrate. The hydrates are useful in the manufacture of numerous absorbent articles. They are especially useful where high capacity is desirable, such as in articles to be worn. Thus, they are particularly useful for diapers and incontinence pads, and also for sanitary napkins, bandages and the like. In diapers, the absorbent hydrates may be used as the sole absorbent or as a component improving the quality of the existing absorbent. In the manufacture of diapers in which the hydrate is incorporated as an improvement to the liquid receiving portion of the diaper, the hydrate is applied to the surface of the aqueous liquid receiving portion of the article, namely batting, and the resulting modified batting provided with moisture impermeable backing and a moisture permeable top sheet. Alternatively, the absorbent hydrate may be coated on a conventional non-absorbent moisture impermeable diaper backing without batting and thereafter laminated with a conventional moisture permeable top sheet to provide a thin diaper.

In the case of sanitary napkins, the hydrates may be applied to the cellulosic absorbent surface and wrapped in a conventional manner to produce a napkin of improved absorbent capacity.

In the case of bandages, the hydrates may be coated onto an aqueous liquid permeable but gel impervious material, e.g. non woven fabrics such as rayon or polyester fabrics, and then inserted in the gauze bandage.

The expression "absorbent" refers to water-insoluble, water-swellable polymers as hereinafter described having an enhanced capacity for removing water or aqueous fluids. The water-insoluble, water-swellable polymers are lighty cross-linked polymers containing a plurality of hydrophilic groups, such as carboxyl, carboxamide, sulfonate salt or hydroxyl groups, along the polymer chain in sufficient porportions so that the polymer would be water-soluble if it were not for the cross-linking thereof. In these polymers, the hydrophilic groups constitute at least 25% and up to 72% of the molecular structure. The materials are of sufficient molecular weight or degree of cross-linking to be water insoluble while being water-swellable. Many of the suitable materials are those which have been reported to have an average molecular weight per cross-linkage in the range of from about 13,000 to about 300,000 but are not limited thereto. The most common and best known of such materials are polyacrylate modified polysaccharides, cross-linked synthetic polyacrylates such as sodium and potassium poly(methacrylates), cross-linked carboxymethylcelluloses or cross-linked poly(alkylene oxides) as hereinafter defined. Other graft polymers of polysaccharides and natural gums such as xantham gum, locust gum, guar gum and the like or blends thereof are also suitable provided they meet the requirements of water insolubility and water swellability. One such polymer is a starch grafted polyacrylate. The water-insoluble, water-swellable polymers have a gel capacity of at least about 10. By "gel capacity" is meant the weight of aqueous fluid which can be imbibed and held per unit weight of polymer, i.e., grams of fluid per gram of polymer. Stated another way, the absorbent polymers have an absorbent capacity of at least 10 times the weight of the material in dry form. The capacity may be up to 1500 times or more of the weight of the material in dry form; commonly it is about 15 to 70 times the dry weight. The materials are frequently spoken of in the art as "hydrogels", "hydrocolloids" or "superabsorbents". Many of the water-swellable polymers are available commercially.

The polymers are used in particulate form. By "particulate form" is meant a substance in the form of fine discrete particles. They may be variously shaped such as spherical, rounded, angular, acicular, irregular, or fibrous. The particles generally range in size from about 1 micron to $2 \times 10^4$ microns in diameter or cross-section (largest dimension when not spherical). The particles are preferably of finely divided powder of particle size of from about 1 to about $10^3$ microns.

The preferred synthetic acrylate polymer absorbents are those which have a salt group, an acid group, or which have both an amide group and a salt or acid group. These have been represented in the literature, e.g. U.S. Pat. No. 3,686,024 incorporated herein by reference.

The invention is not limited to the use of water or saline alone as a treatment medium for the absorbents. Absorbencies of hydrates made according to the invention are not significantly different if water used to wet the superabsorbent is replaced by saline. Other aqueous solutions containing dyes as urine wetness indicators or preservatives to prevent microbiological growth in the aqueous composition may be employed.

In addition to the foregoing components, the composition may have included therein minor amounts of other additives which may impart desirable properties to the absorbent product. Thus, a surface active wetting agent, particularly a non-ionic surface active agent may be included to enhance liquid uptake. A surface active agent is of particular advantage in assisting vertical transport of liquids. Representative surface active agents are those commonly described such as alkyl aryl polyether alcohols or alkyphenyl ethers of polyethylene glycol, e.g. reaction product of 1-octylphenol or nonylphenol with ethylene oxide. Fine fibrous cellulose such as cellulose flour, silicates and the like also have similar effect. Activated charcoal or other adsorbent may be included for odor uptake. Fragrance, coloring, etc. may be included for a pleasing effect. Inert materials containing bound water such as silicates, aluminum hydrate and the like may be employed to modify the texture of the sheet. Similar results may be achieved employing slightly wet ethylene glycol or glycerol, e.g. commercial glycerine. If the absorbent immobilizing composition contains a low level of pulverulent absorbent, there is a slight tendency for the absorbent to settle. The composition may be modified to include small quantities of materials to affect its spreading properties. Suitable viscosity modifiers include silicated powders, clays, zinc oxide, inert fillers and like materials. Generally, the additives, if employed, do not constitute more than about 25% of the total hydrate.

In order to more completely describe the present invention the following Examples are given.

EXAMPLES 1-3

In these Examples absorbent hydrates were prepared by adding water or a 1% aqueous sodium chloride solution (saline) in separate experiments to each of three superabsorbents with stirring. Each hydrate contained about 33% by weight of superabsorbent and 67% by weight of water. The hydrates comprised agglomerated particles of superabsorbent having a slightly tacky texture.

Teabag absorbencies of the hydrates were measured by placing 0.2-0.4 g of hydrate in a teabag, stapling the open end of the bag, immersing the bag in the saline for 10 seconds, recording the uptake in weight of the bag, and also recording uptakes of the same bag at 30 seconds, and 60 seconds. After the 60 second uptake each bag was squeezed by hand until the bag ruptured, and the new uptake recorded in order to determine the capacity of the hydrate to retain absorbed water.

As a control, dry superabsorbent was also subjected to the teabag absorbency test in each case.

Table 1 below summarizes teabag absorbencies of each dry superabsorbent, each superabsorbent hydrate and each superabsorbent hydrate calculated on the basis of the dry powder alone in the hydrate.

TABLE 1

| | Teabag Absorbency ml Liquid/g Absorbent | | | | | | | | | | | |
|---|---|---|---|---|---|---|---|---|---|---|---|---|
| | Example 1 | | | | Example 2 Superabsorbent | | | | Example 3 | | | |
| | poly(potassium acrylate) ARASORB 720 Arakawa Chemical, Inc. Chicago, Ill. | | | | poly(potassium acrylate) ARIDALL 1098 Chemdal Corp. Arlington Hts., Ill. | | | | poly(sodium acrylate) DRYTECH 520 Dow Chemical USA Midland, Mich. | | | |
| | Seconds | | | | Seconds | | | | Seconds | | | |
| | 10 | 30 | 60 | Teabag Squeeze | 10 | 30 | 60 | Teabag Squeeze | 10 | 30 | 60 | Teabag Squeeze |
| Dry | 20 | 25 | 29 | 20 | 40 | 49 | 56 | 43 | 7 | 14 | 21 | 20 |
| 33% Absorbent - 67% H2O | 17 | 21 | 22 | 12 | 18 | 23 | 26 | 21 | 9 | 13 | 20 | 20 |
| based on "dry" Superabsorbent | 51 | 63 | 66 | 36 | 54 | 68 | 78 | 63 | 26 | 39 | 60 | 20 |
| 33% Absorbent - 67% Saline | 13 | 18 | 21 | 13 | 18 | 23 | 26 | 23 | 11 | 18 | 28 | 23 |
| based on "dry" Superabsorbent | 39 | 54 | 63 | 39 | 55 | 69 | 78 | 69 | 33 | 54 | 84 | 69 |

As Table 1 shows, in each Example, the superabsorbent in hydrate form, i.e., based on dry superabsorbent, absorbs more water or saline than the dry superabsorbent alone and retains at least as much liquid after squeezing.

EXAMPLES 4 to 8

In the following Examples four composites each comprising an absorbent hydrate according to the invention were placed between two-one gram layers of fluffed wood pulp and measured for absorbency on a TEFO tester. (Marketing/Technology Service, Inc., Kalamazoo, Mich.). Fluffed wood pulp is used as an absorbent for articles such as diapers. A layer of fluffy wood pulp containing no hydrate (Ex. 4) and a composite containing 0.3 g of dry superabsorbent (Ex. 8) were used as controls. In using the TEFO tester, the composite is subjected to passage of a saline solution under pressure, and the amount of leakage of saline through the composite is determined as a measure of the composite's ability to retain the saline solution. In these Examples, 50 ml of saline solution at 7 ml/sec was poured over each composite on the tester, at pressures of 100 pascals, (pa), 3 Kpa after 5 minutes and 5 Kpa after 10 minutes.

The hydrates of the composites of Examples 5, 6 & 7 contained 0.3 g of superabsorbent and 0.6 g of water prepared as in Examples 1-3. In the case of Example 5, the hydrate was placed in rows between the layers of fluffed wood pulp (Placed in Rows). In Example 6, the hydrate was sprinkled between the layers (Sprinkled). In Example 7, the hydrate was sprinkled between the pulp layer and allowed to stand overnight at room temperature (Sprinkled, Stand). This allows water vapor to either combine with the superabsorbent or escape from it depending on the relative humidity in the room simulating the treatment a commercial diaper would receive in which no attempt is made to seal the diaper and prevent water loss from the diaper during maintenance, distribution or storage. The superabsorbent used in all composites was a poly(potassium acrylate) Arasorb 720 (Arakawa Chem., Inc.).

Table 2 summarizes the results of the testing in terms of overflow and fluid retained by the composite at the three pressures.

TABLE 2

| Wood Pulp Filler Content | Ex. 4 None | Ex. 5 Hydrate Placed In Rows | Ex. 6 Hydrate Sprinkled | Ex. 7 Hydrate Sprinkled Stand | Ex. 8 Dry Super-Absorbent |
|---|---|---|---|---|---|
| @ 100 pa Overflow | 0 | 0 | 0.6 | 0.13 | 1.3 |
| Fluid Retained @ 3 Kpa | 40 | 45 | 45 | 43 | 47 |
| Fluid Retained @ 5 Kpa | 22 | 29 | 28 | 30 | 31 |
| Fluid Retained | 20 | 25 | 25 | 26 | 27 |

As Table 2 shows, all of the above composites containing superabsorbent hydrate hold more fluid under pressure than pulp alone and hold nearly as much fluid as the dry superabsorbent.

We claim:

1. An absorbent hydrate in particulate form and comprising a mixture of
   (a) a particulate water-insoluble, water-swellable absorbent polymer; and
   (b) from 20% to 80% by weight of the total weight of said hydrate of an aqueous liquid.

2. The absorbent hydrate of claim 1 wherein said aqueous liquid is water.

3. The absorbent hydrate of claim 1 wherein said aqueous liquid is saline.

4. The absorbent hydrate of claim 1 wherein said absorbent polymer is a cross-linked polymer containing a plurality of hydrophilic groups selected from the group consisting of carboxyl, carboxamide, sulfonate salt and hydroxyl.

5. The absorbent hydrate of claim 1 wherein said absorbent polymer is a polysodium acrylate or polysodium methacrylate.

6. The absorbent hydrate of claim 1 wherein said absorbent polymer is a polypotassium acrylate or polypotassium methacrylate.

7. The absorbent hydrate of claim 1 wherein said absorbent polymer is a starch grafted polyacrylate or polymethacrylate.

8. The absorbent hydrate of claim 1 wherein said absorbent polymer is a cross-linked carboxy methyl cellulose.

9. An absorbent hydrate in particulate form and comprising a mixture of
   (a) a cross-linked particulate water-insoluble, water-swellable absorbent polymer selected from the group consisting of a polysodium acrylate, a polysodium methacrylate, polypotassium acrylate, polypotassium methacrylate, a starch grafted polyacrylate, a starch grafted polymethacrylate, and carboxy methyl cellulose; and (b) from 20% to 80% by weight of the total weight of said hydrate of an aqueous liquid.

10. The absorbent hydrate of claim 9 wherein said aqueous liquid is selected from the group consisting of water and saline.

11. The absorbent hydrate of claim 9 wherein said aqueous liquid comprises from 30% to 50% by weight of the total weight of said hydrate.

12. An absorbent article containg the absorbent hydrate of claim 1.

13. An absorbent article containing the absorbent hydrate of claim 9.

14. A method for immobilizing a particulate water-insoluble, water-swellable absorbent polymer comprising combining an aqueous liquid with said polymer in an amount sufficient to form a hydrate in particulate form and wherein the aqueous liquid comprises from 20% to 80% by weight of the total weight of said hydrate.

15. The method of claim 14 wherein said aqueous liquid is water.

16. The method of claim 14 wherein said aqueous liquid is saline.

17. The method of claim 14 wherein said absorbent polymer is a cross-linked polymer containing a plurality of hydrophilic groups selected from the group consisting of carboxyl, carboxamide, sulfonate salt and hydroxyl.

18. The method of claim 14 wherein said absorbent polymer is a polysodium acrylate or polysodium methacrylate.

19. The method of claim 14 wherein said absorbent polymer is a polypotassium acrylate or polypotassium methacrylate.

20. The method of claim 14 wherein said absorbent polymer is a starch grafted polyacrylate or polymethacrylate.

21. The method of claim 14 wherein said absorbent polymer is a cross-linked carboxy methyl cellulose.

22. A method for immobilizing a cross-linked particulate water-insoluble, water-swellable absorbent polymer selected from the group consisting of a polysodium acrylate, a polysodium methacrylate, polypotassium acrylate, polypotassium methacrylate, a starch grafted polyacrylate, a starch grafted polymethacrylate, and carboxy methyl cellulose comprising combining an aqueous liquid with said polymer to form a hydrate in particulate form wherein the aqueous liquid comprises from 20% to 80% by weight of said hydrate.

23. The method of claim 22 wherein said aqueous liquid is selected from the group consisting of water and saline.

24. The method of claim 22 wherein said aqueous liquid comprises from 30% to 50% by weight of the total weight of said hydrate.

25. The method of claim 14 wherein said aqueous liquid comprises from 30% to 50% by weight of the total weight of said hydrate.

* * * * *

REEXAMINATION CERTIFICATE (4053rd)

United States Patent
Lesniak et al.

[11] B1 4,826,880
[45] Certificate Issued Apr. 25, 2000

[54] IMMOBILIZING PARTICULATE ABSORBENTS BY CONVERSION TO HYDRATES

[75] Inventors: John M. Lesniak, Hazlet; Franklin Boardman, Englishtown; Wayne G. Koci, Monmouth Junction, all of N.J.; James E. McCann, Warrington, Pa.

[73] Assignee: Johnson & Johnson, Inc., New Brunswick, N.J.

Reexamination Request:
No. 90/005,057, Jul. 31, 1998

Reexamination Certificate for:
Patent No.: 4,826,880
Issued: May 2, 1989
Appl. No.: 07/098,650
Filed: Sep. 21, 1987

[51] Int. Cl.⁷ ..................................................... C08J 9/36
[52] U.S. Cl. .............................. 521/53; 521/55; 427/212; 427/213.3; 427/213.31; 427/213.33; 427/222; 427/385.5; 428/481; 428/482; 428/483; 428/500; 428/507; 428/509; 428/515; 428/516; 428/532; 428/533; 525/63
[58] Field of Search ...................... 521/53, 55; 427/212, 427/213.3, 213.31, 213.33, 222, 385.5; 428/481, 482, 483, 500, 507, 509, 515, 516, 532, 533; 525/63

[56] References Cited

FOREIGN PATENT DOCUMENTS

| 58-36452 | 3/1983 | Japan . |
| 61-97333 | 5/1986 | Japan . |
| 2162525 | 2/1986 | United Kingdom . |

*Primary Examiner*—Samuel A. Acquah

[57] ABSTRACT

The invention relates to absorbent compositions, to methods for handling and immobilizing particulate absorbents, and to absorbent articles produced from the absorbent compositions. Absorbent materials such as cross-linked, water-insoluble and water-swellable particulate polymers are immobilized and safely handled by adding thereto an aqueous liquid such as water or saline in amounts sufficient to form hydrates in which the water comprises from 20% to 80% by weight of the total hydrate. The hydrates may be extruded, sprinkled, or sprayed and can be incorporated into absorbent articles such as diapers and tampons by conventional means. The hydrates unexpectedly increase the total water absorbency of the absorbent on a dry basis.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 14–21 are cancelled.

Claims 1, 9 and 22 are determined to be patentable as amended.

Claims 2–8, 10–13 and 23–25, dependent on an amended claim, are determined to be patentable.

New claims 26–33 are added and determined to be patentable.

1. An absorbent hydrate in particulate form and comprising a mixture of
   (a) a particulate water-insoluble, water-swellable absorbent polymer; and
   (b) from [20] *30%* to 80% by weight of the total weight of said hydrate of an aqueous liquid.

9. An absorbent hydrate in particulate form and comprising a mixture of
   (a) a cross-linked particulate water-insoluble, water-swellable absorbent polymer selected from the group consisting of a polysodium acrylate, a polysodium methacrylate, polypotassium acrylate, polypotassium methacrylate, a starch grafted polyacrylate, a starch grafted polymethacrylate, and carboxy methyl cellulose; and
   (b) from [20] *30%* to 80% by weight of the total weight of said hydrate of an aqueous liquid.

22. A method for immobilizing a cross-linked particulate water-insoluble, water-swellable absorbent polymer selected from the group consisting of a polysodium acrylate, a polysodium methacrylate, polypotassium acrylate, polypotassium methacrylate, a starch grafted polyacrylate, a starch grafted polymethacrylate, and carboxy methyl cellulose comprising combining an aqueous liquid with said polymer to form a hydrate in particulate form wherein the aqueous liquid comprises from [20] *30%* to 80% by weight of said hydrate.

*26. A method of making an absorbent article, comprising the steps of:*
   *immobilizing a particulate water-insoluble, water-swellable absorbent polymer comprising combining an aqueous liquid with said polymer in an amount sufficient to form a hydrate in particulate form and wherein the aqueous liquid comprises from 30% to 80% by weight of the total weight of said hydrate;*
   *providing a substrate comprising fluffed wood pulp;*
   *applying said hydrate in particulate form to said substrate; and*
   *providing the substrate with a moisture impermeable backing and a moisture permeable top sheet.*

*27. A method of making an absorbent article in accordance with claim 26, wherein*
   *said absorbent article is made as a diaper.*

*28. A method of making an absorbent article in accordance with claim 26, wherein:*
   *said absorbent article is made as a sanitary napkin.*

*29. A method of making an absorbent article in accordance with claim 26, wherein:*
   *said step of applying said hydrate in particulate form includes applying said hydrate to said substrate in a predetermined pattern.*

*30. A method of making an absorbent article, comprising the steps of:*
   *immobilizing a cross-linked particulate water-insoluble, water swellable absorbent polymer selected from the group consisting of a polysodium acrylate, a polysodium methacrylate, polypotassium acrylate, polypotassium methacrylate, a starch grafted polyacrylate, a starch grafted polymethacrylate, and carboxy methyl cellulose comprising:*
   *combining an aqueous liquid with said polymer to form a hydrate in particulate form wherein the aqueous liquid comprises from 30% to 80% by weight of said hydrate,*
   *wherein said aqueous liquid is selected from the group consisting of water and saline,*
   *providing a substrate comprising material selected from the group consisting of cellulose, vinyl films, polypropylene, polyester, polyethylene, nylon, metal foils, elastomers, cloth, and nonwovens of various fibers; and*
   *applying said hydrate in particulate form to said substrate.*

*31. A method of making an absorbent article in accordance with claim 30, wherein:*
   *the material comprising said substrate comprises wood pulp.*

*32. A method of making an absorbent article in accordance with claim 31, wherein:*
   *said substrate is a diaper pad.*

*33. A method of making an absorbent article in accordance with claim 31, including:*
   *wrapping said substrate to produce a sanitary napkin.*

* * * * *